United States Patent [19]

Okamoto et al.

[11] 4,402,875
[45] Sep. 6, 1983

[54] SUBSTITUTED TETRASELENAFULVALENES AND HIGH PRESSURE SYNTHESIS THEREOF

[75] Inventors: Yoshiyuki Okamoto, Ft. Lee, N.J.; Piotr S. Wojciechowski, Lodz, Poland

[73] Assignee: Koppers Company, Inc., Pittsburgh, Pa.

[21] Appl. No.: 303,542

[22] Filed: Sep. 18, 1981

[51] Int. Cl.$^3$ .............................................. C07D 345/00
[52] U.S. Cl. ................................................. 260/239 R
[58] Field of Search ..................................... 260/239 R

[56] References Cited

U.S. PATENT DOCUMENTS 4,312,991 1/1982 Engler et al. ..................... 549/35 X
4,312,992 1/1982 Green ................................ 549/35 X

*Primary Examiner*—Nicholas S. Rizzo
*Assistant Examiner*—D. B. Springer
*Attorney, Agent, or Firm*—Donald M. MacKay; Herbert J. Zeh, Jr.; J. Timothy Keane

[57] ABSTRACT

A process is disclosed for one-step preparation of substituted tetraselenafulvalenes by reaction of carbon diselenide with acetylenic compounds under pressures of at least about 1,000 atmospheres. Substituted tetraselenafulvalenes made by this process are useful as precursors to very pure tetraselenafulvalene and are useful in forming complexes with certain inorganic anions to provide charge-transfer salts having very high electrical conductivity.

19 Claims, No Drawings

SUBSTITUTED TETRASELENAFULVALENES AND HIGH PRESSURE SYNTHESIS THEREOF

BACKGROUND OF THE INVENTION

1. Field of the Invention

Preparations of substituted tetraselenafulvalenes from reactions of carbon diselenide with various acetylenic compounds are well known. Of particular interest herein is a one-step method for synthesis of substituted tetraselenafulvalenes from reactions of carbon diselenide with an acetylenic compound under high pressure conditions.

2. State of the Art

Recent findings of the unusual electronic properties of complexes of tetraselenafulvalent (TSeF) have generated increased interest in new synthetic routes for preparation of TSeF and substituted TSeF analogue-compounds. It has been found, for example, that certain substituted TSeF compounds, such as tetramethyltetraselenafulvalene, can complex with inorganic anions, such as $PF_6^-$ and $AsF_6^-$, to form crystalline charge-transfer salts. These salts, in which the substituted TSeF is characterized as the electron-donor cation, exhibit metallic properties over a wide temperature range and reportedly have electrical conductivities among the highest of known organic materials.

The superior electrical properties of these salts, so-called "organic metals", make the salts particularly likely candidates for many solid-state or physical-electronics applications. In such applications, materials of very high purity are usually required. Known preparations of TSeF and substituted TSeF compounds involve multi-step synthetic routes which typically produce TSeF or substituted TSeF compounds in low yields or in relatively impure form.

For example, fulvalene compounds containing selenium in the ring system have been synthesized by reaction of sodium acetylide with carbon diselenide in the presence of selenium metal to provide 1,3-diselenole-2-selone. A subsequent coupling reaction of this selone compound with trimethyl phosphite produced a selenium-containing fulvalene compound in an overall maximum yield of 20 percent (Engler et al., J. Amer. Chem. Soc., 96, 7376 (1974)).

Tetraselenafulvalene has been prepared by reaction of dimethyl acetylenedicarboxylate with ethylene triselenocarbonate to produce a diester-substituted selone compound, which compound when treated with triphenylphosphine yielded tetraester-substituted selenafulvalene. Subsequent treatment of this fulvalene compound with lithium bromide in the presence of hexamethylphosphoramide provided tetraselenafulvalene in about 23 percent overall yield (Lakshmikanthan et al., J. Org. Chem., 41, 882 (1976).

U.S. Pat. No. 3,941,809 to Kaplan et al., describes a selenium-containing fulvalene compound prepared by a multi-step method involving firstly reduction of a selenium-containing five-member ring organic halide to its partially-hydrogenated derivative, which derivative is reacted with anhydrous fluoboric acid to provide a fluoborate, which fluoborate is then deprotonated in the presence of an alkyl tertiary amine to yield a fulvalene compound containing two or four selenium atoms, depending upon the starting organic halide.

SUMMARY OF THE INVENTION

Substituted tetraselenafulvalene compounds are prepared by subjecting a mixture of reactants to a pressure of at least about 1,000 atmospheres, those reactants comprising carbon diselenide and at least one compound containing an acetylenic moiety. The acetylenic compound may be expressed by the general formula $ZC{\equiv}CZ$ wherein each of the Z substituents may be the same or different and is a member selected from the set consisting of the following groups:

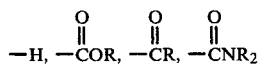

wherein R is selected from hydrogen and alkyl, aryl and alkaryl groups of up to about 12 carbon atoms. Where R is hydrogen in the illustrated structural groups, the Z substituent may be carboxyl group, aldehyde group and amide group, respectively. It is understood that in the amide group structure, each of the two R groups may be hydrogen, alkyl or aryl substituents, or any combination thereof, so as to embrace primary, secondary and tertiary amido groups. The starting compound containing the acetylenic moiety is further characterized by at least one of the Z groups being an electron-withdrawing substituent.

A principal advantage of the present invention is that substituted tetraselenafulvalenes are provided by a one-step reaction, as compared to known synthetic routes requiring complicated multi-step reactions. Moreover, the process of the invention may be carried out in the absence of catalyst. Inasmuch as contaminating catalysts are not required in the present process, substituted TSeF compounds of exceptional purity can be prepared, which compounds are useful as precursors to obtaining very pure tetraselenafulvalene. Moreover, synthesis of troublesome by-products is less likely in the single-step process of the invention as compared to multi-step preparations. High purity TSeF and substituted TSeF compounds are particularly useful in providing an electron-donor cation in charge-transfer salts such as provided by complexes of TSeF and substituted TSeF with inorganic anions such as $PF_6^-$, $AsF_6^-$, $SbF_6^-$, $BF_4^-$ and $NO_3^-$.

DETAILED DESCRIPTION OF THE INVENTION

The terms "high pressure synthesis" or "high pressure reactions" as used herein are intended to describe preparation of fulvalene compounds by subjecting certain reactants to a pressure of at least about 1,000 atmospheres for a time and at a temperature sufficient to form fulvalene compounds. The term "fulvalene compound" is intended to embrace products made by the process of the invention, which products contain the basic structural configuration of tetraselenafulvalene (TSeF) (also known as 1,3-diselenole-(1,3-diselenol-2-ylidene) depicted in formula I:

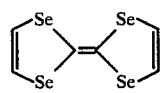

(I)

Such fulvalene compounds may be prepared by processes utilizing the step depicted generally in equation II:

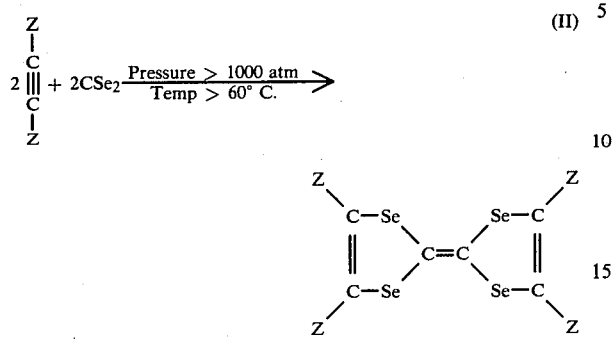

(II)

wherein the Z groups are substituents as defined before. Expected substituted tetraselenafulvalene reaction products will be found as both cis- and trans-isomers. The process is particularly suitable for preparing substituted tetraselenafulvalenes useful as precursors to obtaining relatively pure quantities of tetraselenafulvalene (TSeF).

Preferred acetylenic starting materials for making substituted TSeF compounds include compounds of the general type ZC≡CZ wherein at least one of the Z groups is an electron-withdrawing substituent selected from carboxyl group, carboxyl aliphatic ester groups and amido groups.

Carboxyl and carboxyl aliphatic ester groups suitable as Z substituents may be further defined as members of a class embraced by empirical formula III:

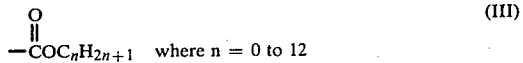

(III)

with such Z substituents being attachable to the TSeF structure at the carbonyl carbon of the Z substituent. Carboxyl group as a Z substituent is typified by carboxyl group contained in formic acid. Carboxyl aliphatic ester groups as the Z substituent are typified by groups contained in the esterification products of formic acid with an aliphatic alcohol of one to about 12 carbon atoms. Representative straight-chain aliphatic alcohols include methyl, ethyl, n-propyl, n-butyl, n-pentyl, n-hexyl, n-heptyl, n-octyl, n-nonyl, n-decyl and n-dodecyl alcohols. Representative branched-chain aliphatic alcohols include isopropyl, isobutyl, sec-butyl, tert-butyl, isopentyl, amyl and tert-pentyl alcohols.

Examples of amido group substituted acetylenic compounds include acetylene carboxamide, acetylene dicarboxamide, propiolic carboxamide, propiolic dimethylcarboxamide, acetylene bis(dimethylcarboxamide), propiolic diethylcarboxamide, propiolic dipropylcarboxamide, acetylene bis(diethylcarboxamide), acetylene bis(dipropylcarboxamide), propiolic dioctylcarboxamide and acetylene bis(dinonylcarboxamide).

Particularly preferred acetylenic starting materials for reacting with carbon diselenide in preparation of substituted TSeF compounds are acetylenic-containing compounds such as methyl propiolate, propiolic acid, dimethyl acetylenedicarboxylate and acetylene dicarboxamide. Substituted TSeF compounds prepared from these starting materials will have structures as shown in Equation II with Z substituents selected from the group consisting of hydrogen,

In the reaction of carbon diselenide with methyl propiolate, or with dimethyl acetylenedicarboxylate, or with a mixture of both esters, as the acetylenic starting material, an intermediate structure is formed as shown in formula IV:

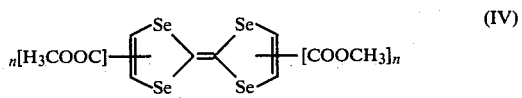

(IV)

wherein "n" may be 1 or 2. Formula IV embraces di, tri, or tetra-ester substituted TSeF compounds including cis- or trans-isomers of such compounds. Such intermediate compound may be treated with lithium bromide in the presence of hexamethylphosphoramide to provide tetraselenafulvalene, as described in the publication of Lakshmikanthan et al., J. Org. Chem. 41, 882 (1976).

In the reaction of carbon diselenide with propiolic acid as the acetylenic starting material, an intermediate is formed having the structure V:

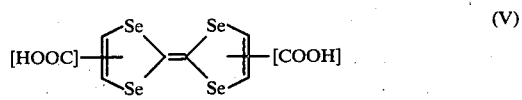

(V)

Formula V embraces di-substituted TSeF compounds including the cis- or trans-isomers. These intermediates may be decarboxylated to tetraselenafulvalene by heating the acid intermediate to 240° C. in pyridine in a sealed vessel, or by treating the acid intermediate with hexamethylphosphoramide in the presence of copper-bronze metal for 20 minutes at 100° C.

In the reaction of carbon diselenide with acetylene carboxamide, or with acetylene dicarboxamide, or with a mixture of both amides, as the acetylenic starting material, an intermediate structure is formed as shown in Formula VI:

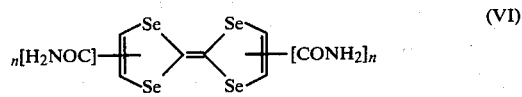

(VI)

wherein "n" may be 1 or 2. Formula VI embraces di, tri, or tetra-amide substituted TSeF compounds including cis- or trans-isomers of such compounds. Such intermediate amide-substituted compounds may be subjected step-wise to firstly alkaline hydrolysis to form a carboxylate salt of the amide-substituted precursor, which salt is acidified with a strong acid to form a carboxylic acid derivative, which derivative may then be decarboxylated to provide TSeF. Decarboxylation may be accomplished by heating the derivative to 240° C. in pyridine in a sealed vessel, or by treating the derivative with hexamethyl-phosphoramide in the presence of copper-bronze metal for 20 minutes at 100° C.

It has been found that effective synthesis of TSeF and substituted TSeF compounds is achieved by a combination of suitable temperature and pressure conditions.

For example, when acetylenic compounds and $CSe_2$ are subjected to pressures as high as 4500 atmospheres, synthesis does not go forward at temperatures around 20° C. Generally, reaction temperatures of at least about 60° C. are required, and temperatures in a range from about 60° C. to about 110° C. are preferred; reaction temperatures in a range from 60° C. to about 90° C. are especially preferred. Reaction temperatures greater than about 120° C. should be avoided inasmuch as unwanted by-products may form at such higher temperatures. While pressures of at least about 1000 atmospheres are generally effective in the described process, reaction pressures of about 2000 atmospheres or greater are preferred.

In order to demonstrate the process of the invention, reactions of carbon diselenide with four acetylenic compounds were carried out under varying reaction conditions of temperature, time and pressure. In all cases except one, good yields of very pure substituted TSeF compounds were obtained under high pressure conditions at reaction temperatures of 60° C. or higher. In the synthesis of TSeF dicarboxylic acid, yield was lower in one high pressure run at a relatively higher temperature, as compared to yields obtained in other high pressure preparations of TSeF dicarboxylic acid and TSeF ester. This one low-yield run may be attributed to decomposition of the TSeF dicarboxylic acid product to TSeF and $CO_2$ inasmuch as $CO_2$ was evolved during the reaction.

The high pressure reactions were run in Teflon capsule having a three-ml capacity. The capsule was mounted in a steel die equipped with a heating band; pressure was applied with a Clifton 200-ton hydraulic press. Acetylenic compound starting materials were obtained from Aldrich Chemical Co., Milwaukee, Wis., and were used as received without further purification. Infrared spectra for reaction products dispersed in KBr pellets were recorded on a Perkin-Elmer Model 457 grating IR Spectrophotometer; melting point determinations were made using an electro-thermal melting point apparatus.

EXAMPLE I

A starting mixture was prepared by dissolving 0.5 g of methyl propiolate (5.9 mmol) and 1.0 g of carbon diselenide (5.9 mmol) in 5 ml of methylene chloride. A three-ml capacity Teflon reaction capsule was filled with a portion of this starting mixture, there being substantially no free-space above the reaction mixture. Pressure was applied to the contents of the reaction vessel and maintained at 5,000 atm.,±200 atm., for a period of about 13 hours, while the temperature was maintained at about 60° C. The capsule was allowed to cool to room temperature over a period of about two hours. The capsule was opened and found to contain a dark brown solid material in contact with a small amount of dark brown liquid. The solid material was isolated from the liquid by filtration, washed several times with small quantities of methylene chloride and then dried under reduced pressure. A dark brown solid material in an amount of 0.64 g was obtained equivalent to a yield of 85 percent, based upon the amount of methyl propiolate used. The dark brown material had a melting point of 156°–161° C. This dark brown material was purified by column chromatography using a silica-packed column eluted with a cyclohexane-benzene mixture. The melting point of the purified material was 160°–162° C. The purified product was identified as 4,4'(5')-bis(carbomethoxy)tetraselenafulvalene, as characterized by the following analytical data:

IR peaks: 1710, 1535, 1430 and 1240 $cm^{-1}$;
NMR: δ3.75 S;
Mass spectrum: m/e 512 (based on $^{80}Se$);

| UV in cyclohexane: | $\lambda_{max}$ (log $\epsilon$) | wavelength (nm) |
|---|---|---|
| | 4.34 | 249 |
| | 4.44 | 254 |
| | 4.44 | 261 |
| | 4.25 | 283 |
| | 3.90 | 326 |
| | 3.47 | 420 |

EXAMPLE II

The high pressure reaction of methyl propiolate and $CSe_2$ was repeated under conditions substantially as set out in Example I, except that the pressure applied was 4,500 atm., the temperature of reaction was 65° C. and the reaction time was about 12 hours. A dark brown solid material was obtained in an amount of 0.66 g, equivalent to a yield of 89 percent. Qualitative determinations of the reaction product confirmed the presence of relatively pure compound identified as 4,4'(5')-bis(-carbomethoxy)tetraselenafulvalene.

EXAMPLE III

A starting mixture was prepared by dissolving 0.9 g of dimethyl acetylenedicarboxylate (6.4 mmol) and 1.0 g of carbon diselenide (5.9 mmol) in 5 ml of methylene chloride. Conditions of reaction were repeated substantially as set out in Example I, above, with a pressure of 5,000 atm.,±200 atm., applied to the contents of the reaction vessel, heated to a temperature of about 60° C. for about 13 hours. A solid material was obtained in contact with a liquid, which solid material was separated by filtration, washed and dried as described before. A dark brown solid material was obtained in an amount of 0.9 g, equivalent to a 90 percent yield based upon the amount of dimethyl acetylenedicarboxylate used. This material was found to have a melting point of 139°–143° C. The material was then purified by column chromatography using a silica-packed column eluted with a cyclohexane-benzene mixture. The melting point of the purified material was 144°–145° C. The product was identified as 4,4',5,5'-tetrakis(carbomethoxy)tetraselenafulvalene, as characterized by the following analytical data:

IR Peaks: 1720,1565,1435,1275 and 1250 $cm^{-1}$;
NMR: δ3.83 S;
Mass spectrum: m/e 628 (based on $^{80}Se$);

| UV in cyclohexane: | $\lambda_{max}$ (log $\epsilon$) | wavelength (nm) |
|---|---|---|
| | 4.40 | 260 |
| | 4.43 | 285 |
| | 3.70 | 328 |
| | 3.56 | 422 |

EXAMPLE IV

The high pressure reaction of dimethylacetylene dicarboxylate and carbon diselenide was repeated under conditions substantially as set out in Example III except that the pressure applied was 4500 atm., the temperature of reaction was about 65° and the reaction time was about 12 hours. A dark brown solid material was isolated in an amount of 0.42 g, equivalent to a yield of 92 percent. Qualitative determinations of the reaction product confirmed the presence of relatively pure compound identified as 4,4',5,5'-tetrakis(carbomethoxy)tetraselenafulvalene.

EXAMPLE V

A starting mixture was prepared by dissolving 0.5 g of propiolic acid (7.1 mmol) in 5 ml of methylene chloride. To this mixture was added 1.0 g of carbon diselenide (5.9 mmol). Conditions of reaction were repeated substantially as set out in Example I, above, with a pressure of 5000 atm., ±200 atm., applied to the contents of the reaction vessel heated to a temperature of about 60° C. for about 15 hours. Upon opening of the reaction vessel after cooling to room temperature, $CO_2$ gas was found to have evolved from the reaction mixture. A brown solid material was removed from the capsule, and then treated sequentially by the steps of washing with methylene chloride, dissolving 1 N NaOH, filtering, acidifying with 2 N HCl, and then drying the product overnight under reduced pressure at 60° C. A dark brown solid material was obtained in an amount of 0.47 g, equivalent to a yield of 62 percent based upon propiolic acid starting material. The product, characterized by IR peaks at 3500, 1670, 1540 and 1380 cm$^{-1}$, was identified as tetraselenafulvalene-4,4'(or 5')-dicarboxylic acid. The acid product was further treated by decarboxylation to tetraselenafulvalene by suspending the acid in hexamethylphosphoramide in the presence of a trace amount of copper-bronze metal and then heating this mixture at about 100° C. for about 20 minutes (see precise decarboxylation procedures set out in Lakshmikanthan et al., J. Org. Chem., 45, 2632 (1980)). The reaction product was identified as tetraselenafulvalene as characterized by the following analytical data:

| UV in cyclohexane: | $\lambda_{max}$ (log $\epsilon$) | wavelength (nm) |
|---|---|---|
| | 4.10 | 287 |
| | 4.10 | 300 |
| | 3.15 | 364 |
| | 2.10 | 500 |

EXAMPLE VI

A starting mixture was prepared by dissolving 0.5 g of acetylene dicarboxamide (4.4 mmol) in 5 ml of dimethyl formamide with mild heating. To this mixture was added 1.9 g of carbon diselenide (5.9 mmol). A three-ml capacity Teflon reaction capsule was filled with a portion of this starting mixture, there being substantially no free-space above the reaction mixture. Pressure was applied to the contents of the reaction vessel and maintained at 5,000 atm., ±200 atm., for a period of about 15 hours, while the temperature was maintained at about 65° C. The capsule was allowed to cool to room temperature over a period of about two hours. The capsule was opened and found to contain a mixture of brown solid material in contact with a small amount of dark brown liquid. The solid material was isolated from the liquid by adding the mixture to water, from which the solid material precipitated. The material was then removed by filtration and washed with small quantities of ethyl ether, and then dried under reduced pressure. A dark brown solid material was obtained in an amount of 0.76 g equivalent to a yield of 85 percent based upon the amount of amide starting material. After recrystallization of the brown material from acetone solvent, a brown solid material was obtained having a decomposition point of 230° C. The brown product, characterized by IR peaks at 3300–3100, 1640, 1570, 1370, 1250, 960 and 880 cm$^{-1}$, was identified as 4,4',5,5'-tetrakis(carboxamide)tetraselenafulvalene.

Although specific examples of the instant invention have been set forth hereinabove, it is not intended that the invention be limited solely thereto, but is to include all the variations and modifications falling within the scope of the appended claims.

What is claimed is:

1. A process for preparing a fulvalene compound, said process comprising the step of subjecting a mixture of reactants to a pressure of at least about 1,000 atmospheres, for a time and at a temperature sufficient to form said fulvalene compound, said reactants consisting essentially of carbon diselenide and an acetylenic compound of the formula $$ZC \equiv CZ$$

wherein one of the Z substituents is a member selected from

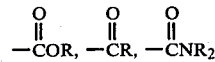

and the remaining Z substituent is the same or hydrogen; wherein R is selected from hydrogen and normal alkyl, of up to 12 carbon atoms.

2. The process of claim 1 wherein said Z substituent is selected from carboxyl and carboxyl alkyl ester groups defined by the empirical formula

where n = 0 to 12.

3. The process of claim 1 wherein the fulvalene compound is a substituted tetraselenafulvalene and said acetylenic compound is methyl propiolate, propiolic acid, dimethyl acetylenedicarboxylate, or acetylene dicarboxamide.

4. The process of claim 3 wherein the step of subjecting a mixture of carbon diselenide and methyl propiolate to a pressure of at least about 4,000 atmospheres provides an intermediate having the structure

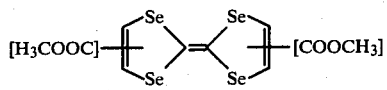

5. The process of claim 4 wherein said intermediate is subjected to alkaline hydrolysis to form a salt, which salt may be subjected to acid hydrolysis to form a carboxylic acid derivative, which carboxylic acid derivative may be subjected to decarboxylation to form tetraselenafulvalene.

6. The process of claim 3 wherein the step of subjecting a mixture of carbon diselenide and propiolic acid to a pressure of at least about 4,000 atmospheres provides an intermediate having the structure

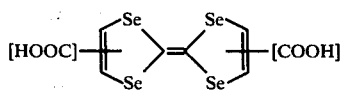

7. The process of claim 6 wherein said intermediate is subjected to decarboxylation to form tetraselenafulvalene.

8. The process of claim 3 wherein the step of subjecting a mixture of carbon diselenide and dimethyl acetylenedicarboxylate to a pressure of at least about 4,000 atmospheres provides an intermediate having the structure

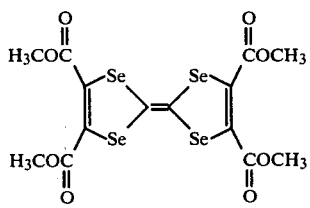

9. The process of claim 8 further characterized by treating said intermediate with lithium bromide in the presence of hexamethylphosphoramide to form tetraselenafulvalene.

10. The process of claim 3 wherein the step of subjecting a mixture of carbon diselenide and acetylene dicarboxamide to a pressure of at least about 4,000 atmospheres provides an intermediate having the structure

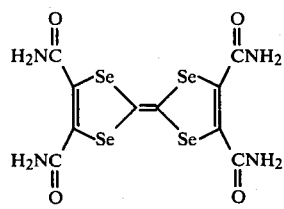

11. The process of claim 10 wherein said intermediate is subjected to alkaline hydrolysis to form a salt, which salt may be subjected to acid hydrolysis to form a carboxylic acid derivative, which carboxylic acid derivative may be subjected to decarboxylation to form tetraselenafulvalene.

12. The process of claim 1 wherein the temperature of said reactants is maintained at about 60° C. or higher.

13. A substituted tetraselenafulvalene having the formula

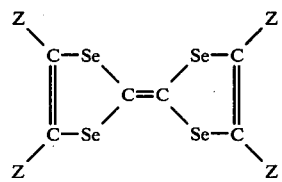

prepared by a process comprising the step of reacting carbon diselenide with a compound having the formula

ZC≡CZ wherein one of the Z substituents is a member selected from

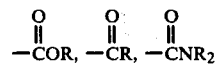

and the remaining Z substituent is the same or hydrogen; wherein R is selected from hydrogen and normal alkyl, having up to 12 carbon atoms; said reacting step performed under a pressure of at least about 1000 atmospheres and for a time and temperature sufficient to form said substituted tetraselenafulvalene.

14. The substituted tetraselenafulvalene in claim 13 wherein said acetylenic compound has at least one Z group selected from a class defined by the empirical formula

wherein n=0 to 12.

15. A substituted tetraselenafulvalene having the formula

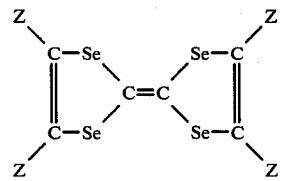

wherein at least one of the Z substituents is selected from the group consisting of

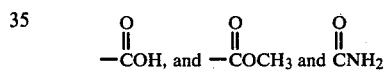

and the remaining substituents are the same or hydrogen; said substituted tetraselenafulvalene prepared by a process comprising the step of reacting carbon diselenide with a compound selected from the group consisting of propiolic acid, methyl propiolate, dimethyl acetylenedicarboxylate, and acetylene dicarboxamide; said reacting step performed under a pressure of at least about 1000 atmospheres and at a temperature and for a time sufficient to form said substituted tetraselenafulvalene.

16. 4,4′(or 5′)-Bis(carbomethoxy)tetraselenafulvalene prepared by a process comprising the step of reacting carbon diselenide and methyl propiolate under a pressure of at least about 2,000 atmospheres and at a temperature of at least about 60° C.

17. 4,4′,5,5′-Tetrakis(carbomethoxy)tetraselenafulvalene prepared by a process comprising the step of reacting carbon diselenide and dimethyl acetylenedicarboxylate under a pressure of at least about 2,000 atmospheres and at a temperature of at least about 60° C.

18. Tetraselenafulvalene-4,4′(or 5′)-dicarboxylic acid prepared by a process comprising the step of reacting carbon diselenide and propiolic acid under a pressure of at least about 2,000 atmospheres and at a temperature of at least about 60° C.

19. 4,4′,5,5′-tetrakis(carboxamide)tetraselenafulvalene prepared by a process comprising the step of reacting carbon diselenide and acetylene dicarboxamide under a pressure of at least about 2,000 atmospheres and at a temperature at least about 60° C.

* * * * *